United States Patent [19]

McCarthy

[11] Patent Number: 5,480,642
[45] Date of Patent: * Jan. 2, 1996

[54] SYNTHETIC IMMUNOREGLATORS, AND METHODS OF USE AND PREPARATION

[75] Inventor: Robert E. McCarthy, Omaha, Nebr.

[73] Assignee: The Board of Regents of the University of Nebraska, Lincoln, Nebr.

[*] Notice: The portion of the term of this patent subsequent to May 20, 2003, has been disclaimed.

[21] Appl. No.: 224,191

[22] Filed: Jul. 21, 1988

Related U.S. Application Data

[63] Continuation-in-part of Ser. No. 809,290, Dec. 16, 1985, abandoned, which is a continuation-in-part of Ser. No. 451,016, Dec. 20, 1982, Pat. No. 4,590,181.

[51] Int. Cl.$^6$ .......................... A61K 45/00; A61K 31/715
[52] U.S. Cl. ............................................ 424/278.1; 514/54
[58] Field of Search .................................. 424/92, 204.1, 424/278.1; 514/885, 54

[56] References Cited

U.S. PATENT DOCUMENTS

| | | | |
|---|---|---|---|
| 4,066,829 | 1/1978 | Nair. | |
| 4,185,090 | 1/1980 | McIntire | 536/1.1 X |
| 4,260,602 | 4/1981 | Moreno | 536/1.1 X |
| 4,590,181 | 5/1986 | McCarthy | 514/54 |

OTHER PUBLICATIONS

Yokochi et al. "Suppression of B–Memory Cell Function by . . ." Immuno biol; vol. 158, 454–466 1981.
Mitsuya et al "Dextran sulfate suppression of virus in HIV . . ." Science vol. 240 646–649 (Apr. 29, 1988).
Bona "Mitogenic . . ." J. Exp. Med. 148(1):136–147 (1978).
Goodman "The Pharmacological Basis of Therapeutics" 7th ed. 1985.
Bellavia "Effects of . . . " Immunopharmacology 13(1987) 173–180.
Merck Manual of Diagnosis and Therapy Berkow, Editor, 15th Ed. 1987.
McCarthy et al., Immunology, vol. 32: 963–974 (1977).
Schweiger, Carb. Res., 21: 219–228 (1972).
Stanier et al., The Microbiol World, 4th Ed., Prentice–Hall, Englewood, 1976, p. 323.

Primary Examiner—Raymond Henley, III
Attorney, Agent, or Firm—Zarley, McKee, Thomte, Voorhees & Sease

[57] ABSTRACT

To regulate the immune response to an antigen, a subject with the antigen is injected with polyanionic polysaccharide derivative: (1) having a molecular weight of between 1,000 and 600,000; (2) selected to correspond to the antigen; (3) not being cytotoxic at an effective dosage; and (4) stimulating a cell-mediated immune response. For virus, as an example, mycodextran sulfate or pustulan sulfate may be used in sufficient quantities to stimulate cell-mediated immune responses without stimulating synthesis of gamma-E globulin and gamma-G globulins. The polyanionic polysaccharide derivative may be injected alone to stimulate cell-mediated immune responses to antigens in a diseased subject.

5 Claims, No Drawings

SYNTHETIC IMMUNOREGLATORS, AND METHODS OF USE AND PREPARATION

REFERENCE TO RELATED APPLICATIONS

This application is a continuation-in-part of U.S. application Ser. No. 06/809,290, filed Dec. 16, 1985, now abandoned, which is a continuation-in-part application of U.S. application Ser. No. 06/451,016, now U.S. Pat. No. 4,590,181, for Synthetic Immunoregulators and Methods of Use and Preparation filed by Robert E. McCarthy on Dec. 20, 1982, and assigned to the same assignee as this application.

BACKGROUND OF THE INVENTION

This invention relates to immunoregulators and their methods of use and preparation.

It is known to use synthetic adjuvants or immunoregulators. However, the selection of such regulators has been experimental and not based on sound theoretical principles because several factors necessary for such selection were not understood, such as: (1) the exact mechanism for the immune response; (2) if T-cells or B-cells or both T-cells and B-cells were involved; (3) the manner in which regulators interact with the immune system for a specific response; and (4) the manner in which compounds or mixtures can be synthesized to enable them to elicit the desired response.

A prior art synthetic adjuvant, dextran sulfate, has a polysaccharide molecule with anionic groups attached. The use of dextran sulfate as an adjuvant was disclosed in McCarthy, R. E., Arnold, L. W., and Babcock, G. F.: "Dextran Sulfate: An Adjuvant for Cell-Mediated Immune Responses, "*Immunology*, 32:964, 1977. The immune response was based upon trial and error and it was not known if it would stimulate a T-cell response without a B-cell response. It stimulated both T-cell response and B-cell response.

Thus, prior art techniques and adjuvants have had several disadvantages, such as: (1) they are not predictable except by trial and error; (2) new adjuvants cannot be easily discovered or synthesized; (3) it is difficult to know the best manner and time of using them; (4) they are not usable to elicit only certain responses such as to select one that stimulates a T-cell response but does not stimulate antibody synthesis; and (5) many of them are cytotoxic in effective dosages.

SUMMARY OF THE INVENTION

Accordingly, it is an object of this invention to provide novel synthetic immunoregulators.

It is a further object of the invention to provide a novel technique for obtaining, using and preparing synthetic immunoregulators.

It is a still further object of the invention to provide a novel technique for the use of synthetic immunoregulators to study specific immune reactions.

It is a still further object of the invention to provide a novel method for immunizing patients or animals.

It is a still further object of the invention to provide a novel method for using synthetic immunoregulators to regulate immune responses.

It is a still further object of the invention to provide a novel technique for enhancing cell-mediated immune responses without stimulating the synthesis of gamma-E globulin or gamma-G globulins.

It is a still further object of the invention to provide a novel technique for enhancing cell-mediated immune responses with reduced probability of anaphylactic shock reactions.

It is a still further object of the invention to provide a novel technique for specifically enhancing cell-mediated immune responses without simultaneously stimulating synthesis of immune globulins G and immune globulin E.

It is a still further object of the invention to provide a novel technique for utilizing a regulator that selectively regulates only one of the actions of T-cells or B-cells in the immune response.

It is a still further object of the invention to provide a novel technique for utilizing an adjuvant that is incorporated into a viral vaccine so as to minimize anaphylactic shock reactions.

It is a still further object of the invention to provide a novel method of synthesizing immunoregulators by substituting chemical anionic groups onto a high-molecular-weight backbone of a compound that is not regulatory to selectively arrive at a regulator which causes a predetermined stimulating response.

It is a still further object of the invention to provide a novel technique for selecting certain derivatives of polysaccharide compounds which affect the humoral and cellular immune responses in a predetermined manner.

It is a still further object of the invention to provide a novel technique for controlling the humoral hemagglutinating antibody responses (IgM and IgG) of animals and the responses of the classes of immunoglobulin E and $G_1$ which are associated with anaphylactic reactions.

It is a still further object of the invention to provide a novel technique for synthesizing compounds to cause specific immunoregulatory effects.

It is a still further object of the invention to provide novel high-molecular-weight sulfate compounds which have known immunoregulatory effects.

In accordance with the above and further objects of the invention, the immune response of a subject to an antigen is regulated by an injection of a synthetic immunoregulator in sufficient amount to provide a selected type and degree of immune response in the subject. The synthetic immunoregulator includes a high-molecular-weight compound, which is not by itself regulatory, but following the addition of anionic groups on it, interacts with specific lymphocytes. The high-molecular-weight compound may be a polysacchaaride and the interacting groups may be anionic groups, such as sulfate. If they are sulfates, the polysaccharide should be sulfated to provide at least two sulfate groups.

The synthetic immunoregulators are not cytotoxic at effective doses and have high specific binding values. The polysaccharide and ionic groups, because of their specific binding sites, may provide selective, specific regulatory effects on immune response without excessive toxicity. They may be selected to have a time of effectiveness long enough to permit intermittent doses, such as every two to four weeks. Because of the time span between doses, the synthetic immunoregulator is economical for treatment of chronic diseases by stimulating the appropriate immune response for a long term with reasonably spaced intervals. The intervals should be at least one week long. Moreover, rejection of foreign bodies such as prosthetic devices, skin grafts or the like, may be regulated to some extent.

As can be understood from the above summary, the immunoregulators of this invention and its methods of use and preparation have several advantages, such as: (1) they can be used for T-cell-mediated responses only and thus avoid anaphylactic shock; (2) specific synthetic regulators are available to operate in a predictable manner; (3) it is possible to use a dosage and regulator for a known type of response; and (4) it is possible to synthesize regulators for use with particular antigens.

SPECIFIC DESCRIPTION

Broadly, a novel regulator is provided which stimulates a specific immune response without stimulating other unnecessary immune responses and thus reduces undesirable effects that might be caused by the administration of the immunizing dose of antigen.

The regulator (referred to in the art at times as an adjuvant implying only enhanacement of immune response) is administered in conjunction with the administration of an antigen or by itself to stimulate the immune response to an antigen already in the subject such as cancer cells or intracellular infecting organisms such as *M. liprae* or HIV virus (AIDS). It may be administered in any conventional manner such as by inoculation or orally but preferably by inoculation.

It may be used to regulate response to foreign bodies such as prosthetic devices or skin grafts so as to reduce rejection problems. While the regulators are referred to as stimulating a response, it is believed that they may, under some circumstances, suppress an immune response. The regulators may also inhibit the suppressive effects on the cell mediated immune response exerted by certain agents such as some pathogens and tumor cells.

The synthetic immunoregulators are not cytotoxic at effective doses and have specific binding properties. The polysaccharide and ionic groups, because of their specific binding sites, may provide selective, specific regulatory effects on immune response without excessive toxicity. They may be selected to have an effective time long enough to permit intermittent doses, such as every two weeks, so as to be economical for treatment of chronic diseases by stimulating the appropriate immune response for a long term with reasonably spaced intervals. For example, pustulan sulfate may be an effective treatment for chronic diseases caused by intracellular parasites such as *M. liprae* because it is not cytotoxic at effective doses, stimulates cell-mediated immune response without stimulating gamma-immunoglobulin or E immunoglobulin responses, and continues to be effective in the subject for two weeks.

In one embodiment, regulators enhance cell-mediated immune responses without stimulating synthesis of gamma-E globulin and gamma-G globulin. Since the cell-mediated immune responses are the effective mechanisms against vital diseases and the gamma-G globulin and the gamma-E globulin classes of immunoglobulin cause anaphylactic shock reactions, the regulator increases the effectiveness of immune injections against viruses without creating shock effects. Moreover, certain regulators may be selected to enhance one cell-mediated immune response and not another such as shown by enhancing footpad swelling responses without affecting allograft rejection.

Derivatives of the polysaccharide are used which show specific binding to the lymphatic system, as determined by the techniques described in the publication by Paul, Marangus and Skulmick, 1981 "The Benzodiazepene. GABA— Chloride Ionophase Receptor Complex: Common Site of Minor Tranquilizer Action," *Biol-Psychi* 16(3):213–229, the disclosure of which is incorporated herein by reference with appropriate modification as described in the examples of this case. Dosages are used which are not toxic but effective to enhance a selected immune response.

To prepare the regulator, certain active groups and high-molecular-weight compounds which are not regulatory are selected and the groups attached to convert the high-molecular-weight compound from an immunologically inert compound to a compound that exerts regulatory effects on the immune response system by specific binding. For example, certain polyanionic groups on polysaccharides having molecular weights of between 1,000 and 600,000 have been shown to stimulate T-cells selectively. Sulfation of such high-molecular-weight compounds has provided effective regulators. The resulting regulator has an effect that reflects both the high-molecular-weight backbone and the nature and the amount of the attached group and the selection is made to achieve a desired result taking all three of these factors into consideration.

Polysaccharides that are either inert when tested in their unsulfated condition or which produce minimal immunological response changes are active immunoregulators following sulfation. The degree of sulfation can be modulated so that: (1) some compounds have saturation of all available sites that accept the sulfate; and (2) some compounds have partial sulfation. When modulated, complete sulfation results in the greatest immunoregulatory effect while moderate sulfation yields a lesser immunoregulatory effect.

The polysaccharide sulfate derivatives stimulate cell-mediated T-cell-dependent immune responses without stimulating antibody-mediated immune responses that are B-cell dependent. Certain unmodified polysaccharides stimulate only B-cells and other materials are known which under certain conditions stimulate B-cell and T-cell responses to different degrees. Consequently, the proper approach may be selected and used according to the needs of the subject under certain circumstances.

Cell-mediated immune stimulation increases as the number of sites for each unit of backbone molecule that is bound to an anionic group increases without an increase in B-cell stimulation. For purposes of this discussion: (1) T-cell response is a delayed sensitivity reaction of more than ten percent of a control usually 18 to 24 hours after challenge; and (2) B-cell response is a sensitivity reaction earlier than or four hours after challenge that is more than ten percent of a control.

Two compounds which provide an adequately large molecular backbone for formulation into selective T-cell adjuvants are mycodextran and pustulan. Mycodextran consists of a polymer of D-glucosyl residues with alternating alpha (1–4) and alpha (1–3) linkages. A method of synthesizing mycodextran is disclosed by E. T. Reese and Mandels, *Canadian Journal of Microbiology*, v. 10, p. 103, 1964. Pustulan is a polysaccharide of 20,000 median molecular weight consisting of D-glucosyl residues with beta (1–6) linkages and 2.2 sulfate groups for each anhydrous glucose unit as made by the method described by Schweiger, R. G. 1972 "Polysaccharide sulfate. I. Cellulose Sulfate with a High Degree of Substitution. *Carb. Res.*, 21:219–228, the disclosure of which is incorporated herein.

More specifically, a polysaccharide having a molecular weight of between 1,000 and 600,000 is selected. The polysaccharide can be postulan or micodextran or substantially any other polysaccharide fitting this criteria. The selection is partly by trial and error as will be explained hereinafter.

The polysaccharide is sulfonated or acylated by any conventional means but the degree of sulfonation or acylation is controlled. Samples with different degrees of sulfonation or acylation have differing immunoregulatory effects. Hypersensitivity testing may be done by standard delayed foot pad swelling reaction.

In the alternative, instead of sulfonating the polysaccharide, it may be acylated. The degree of acylation or sulfonation is determined by preparing samples with different reaction times and testing them for immunoregulatory effect until the reaction time required for a suitable level of sulfonation or acylation is determined. Generally, the compound used is of the structural formula shown in formula 1, where R is a monosacchride and it equals a number of individual. monosacchrides of between 60 and 3,600. The unsubstituted carboxyl units are indicated by X and are equal in number to up to 58 or between 58 and 0 and the number of sulfate ions substituted as indicated by Y are between 2 and 3,600.

EQUATION 1

The invention is illustrated by the following examples:

EXAMPLES

GENERAL

In tests for selective enhancement of cell-mediated response without antibody-mediated response, examples 1–7, two different basic polysaccharide backbone molecules were selected for use which varied in the degree of rigidity of the molecule. Two different anionic groups for binding and four control compounds were selected. The polysaccharides are mycodextran and pustulan and the anionic groups were acetyl and sulfate.

For each polysaccharide backbone either acetyl or sulfate groups were attached. The degree of sulfation was modulated in such a way that the compounds were tested with: (1) saturation of all available sites that accept the sulfate or (2) with partial sulfation.

Two methods of sulfation of the polysaccharides were used. Both involved the DMF-S03 complex. In one method, the complex was prepared first and added to the polysaccharide suspended in DMF as described by R. G. Schweiger, *Carb. Res.* 21 (1972) 219–228. In the other method liquid S03 was added slowly (Sulfan B) to a cooled suspension of the polysaccharide in DMF (N, N-Dimethylformamide). Product isolation is also different from that described by Schweiger in that a dialysis step was added and the product was obtained by lyophilization. A similar method was used for acylation.

Three strains of mice were used for all studies except one done on one strain of rats as a control. The strains of mice are: (1) B6D2F1/J (Jackson Laboratories, Bar Harbor, Maine); (2) CFW (Charles River, Wilmington, Mass.); and (3) ESP (Eppley Cancer Institute, Omaha, Nebr.). The strain of rats is COBS COF. On day seven, blood was collected by bleeding from the retroorbital venous plexus.

Candidate immunoregulators were evaluated by the footpad swelling assay. The antigen used was sheep red blood cells (SRBC) obtained from Colorado Serum Company in Denver, Colo. The SRBC were washed three times in Hank's balanced salt solution (HBBS) and resuspended to a concentration of ten percent of the volume of SRBC in HBBS v/v (volume-to-volume percentage). The immunoregulators were dissolved in HBBS and mixed with an equal volume of the SRBC to give a final concentration of five percent SRBC and the desired concentration of the immunoregulator.

The control group of mice were sensitized subcutaneously (s.c.) with five percent SRBC and the appropriate concentration of the immunoregulator. All the solutions were made just prior to sensitization. In the event that the immunoregulators were lytic for SRBC, they were injected uncombined at the same site one after the other at the same time, the immunoregulator being administered first.

Blood was collected by retroorbital venous puncture on days seven and fifteen post sensitization and the mice were challenged in the footpads with 0.05 ml of twenty percent SRBC (in HBSS). The right footpad received the SRBC suspension; the left foot20 pad received an equal amount of phosphate-buffered saline. The thickness of the footpads was measured at 4, 24 and 48 hours after challenge. The difference between the left and right footpads of each mouse was expressed as a percentage. The average percent footpad swelling (APFS) for each group of mice was determined by dividing the sum of the individual swellings by the number of mice in the group. The average percentage increase (API) was determined by subtracting the APFS of the control group from the APFS of the treated group.

The following steps were followed in this procedure:

1. Regulatory Compounds

The polysaccharide-compound regulators are: (1) mycodextran; (2) sulfated mycodextran; (3) pustulan; (4) sulfated pustulan; and (5) acylated pustulan.

2. Toxicity Studies and Dose Determination

Preliminary toxicity studies were performed to determine concentration of the regulators which can be tolerated by the mice. Only doses of adjuvants which do not exhibit systemic or local toxic effects were used in the assays. In examples 1–9 infra, four groups of five mice each were injected with a range of doses of candidate regulators and observed for seven days for gross toxic effects. Animals were sacrificed, autopsied and examined for localized toxic effects.

More specifically, four groups of five mice each were injected subcutaneously with 25 mg, (milligrams) 50 mg, 100 mg, and 200 mg of pustulan sulfate per kilogram of body weight and observed for seven days. Surviving animals were then sacrificed and autopsies performed. The dose used in following experiments was one at which no systemic or local toxic effects were noted.

3. Immediate and Delayed Hypersensitivity Reactions

Mice were immunized with sheep red blood cells (SRBC) with or without regulators. Mice were sensitized on day zero subcutaneously in the scruff of the neck. Groups of ten mice each were injected with two doses of regulator compound and 0.02 milliliter per gram body weight of five percent SRBC in a carrier, or in other words, five percent of the total volume of SRBC and carrier in volume of SRBC added (v/v). Control mice received only the SRBC. Mice of both sexes were used.

The blood from mice of the same group was pooled and the serum used to determine hemagglutinin titers. On day eight, the mice were challenged in the right hind footpad with 0.05 milliliter of a twenty percent (v/v) suspension of SRBC in phosphate-buffered saline (PBS) and in the left hind footpad with 0.05 milliliter of PBS only. The thickness of the footpads was measured at 4, 24 and 48 hours with Vernier calipers after challenge. Bleeding and challenge were repeated on days fifteen and sixteen, respectively.

The difference in thickness between the left and right footpads of each mouse was expressed as a percentage. The average percent footpad swelling (APFS) for each group of mice was determined by dividing the sum of the individual swellings by the number of mice in the group. Significance was determined using the Student's t-test at ninety-five percent confidence limits as described by G. W. Snedecor and W. G. Cochran, 1967, *Statistical Methods*, Iowa State University Press, Ames, Iowa.

Positive footpad swellings occurring at four hours are immediate-type hypersensitivity reactions (antibody-mediated). Positive reactions occurring at 24 and 48 hours are delayed-type hypersensitivity reactions (cell-mediated).

4. Hemagglutinin Titers

Antibody responses of the IgM and IgG classes against SRBC in immunized mice were determined using the microtiter method. All tests were performed in V-bottom microtiter plates (Cooke Engineering Co., Alexandria, Va.). Two-fold dilutions of sera (obtained as described above) were made in bovine serum albumin saline (BSA) (100 milligrams in 100 milliliters PBS). The titer was considered to be the reciprocal of the highest dilution showing positive agglutination. Hemagglutinating antibody titers were determined using the procedure described by McCarthy et al 1977, "Dextram Sulfate: An Adjuvant for Cell Mediated Immune Responses, *Immunology*, 32:9637, 1977.

5. Study of $IgG_1$ and IgE Responses

Two types of experiments were conducted to study the responses of immunoglobulin associated with anaphylactic shock reactions. The first of these is active systemic anaphylaxis, which detects both IgG1 and IgE simultaneously and the second one is passive cutaneous anaphylaxis, which allows a determination of the presence or absence and relative concentrations of IgG1 and IgE in animals that respond.

6. Active Systemic Anaphylaxis

Groups of ten mice were immunized subcutaneously on day zero with fifty micrograms of ovalbumin with or without the candidate adjuvant. Two doses of adjuvant were used and a third group received antigen only. On day fourteen, the mice were challenged intravenously with one milligram of ovalbumin and observed for four hours. The number of mice dying within this time was recorded and the percent of anaphylactic shock determined as the number of deaths divided by the number challenged. This protocol and dosage of antigen has been shown to result in predominantly IgE responses in mice. There is, however, some IgGl produced.

7. Passive Cutaneous Anaphylaxis (PCA)

Groups of ten mice were immunized with ovalbumin and the candidate adjuvant. The mice were bled from the retroorbital venous plexus fourteen days following immunization. The sera were titrated for IgGl and IgE levels using PCA reactions at 2 and 48 hours, respectively, following intradermal injection of serum. Mice were challenged intravenously on day eighteen with one milligram of ovalbumin to assess systemic active anaphylaxis.

EXAMPLE 1

NON-ACYLATED PUSTULAN

The dosage of pustulan was determined in toxicity studies as described under the heading "2. Toxicity Studies" above and the dosage was selected to be one hundred milligrams per kilogram of body weight of the mice. Three strains of mice were used, as shown in Table 1, five male and five female of each strain.

The immediate- and delayed-type hypersensitivity reactions were determined as described under the heading "3. Immediate and Delayed Hypersensitivity Reactions" above. The results are shown in Table 1, in which a "0" (zero) indicates that the footpad swelling was less than ten percent over the control, a "+" (plus) sign means that there was significant footpad swelling greater than ten percent over the control and a "−" (minus) sign means there was a significant suppression of footpad swelling greater than ten percent over the control.

The hemagglutinin titers were determined using the procedure described under the heading "4. Hemagglutinin Titers". The results are shown in Table 1.

EXAMPLE 2

ACYLATED PUSTULAN

The dosage of acylated pustulan was determined in toxicity studies as described under the heading "2. Toxicity Studies" above and the dosage was selected to be one hundred milligrams per kilogram of body weight of the mice. Three strains of mice

TABLE 1

| | NON-ACYLATED PUSTULAN (used at 100 mg/kg body weight) | | | | | |
|---|---|---|---|---|---|---|
| | | First Challenge | | | Second Challenge | | |
| Strain | Sex | 4 hr | 24 hr | 48 hr | 4 hr | 24 hr | 48 hr |
| ESP | M | 0 | + | 0 | 0 | 0 | + |
| ESP | F | 0 | + | + | + | + | + |
| CFW | M | 0 | + | 0 | 0 | 0 | 0 |
| CFW | F | 0 | 0 | 0 | 0 | + | 0 |
| B6D2F1 | M | 0 | + | + | + | + | 0 |
| B6D2F1 | F | Strain Not Available Presently | | | | | |

Hemagglutinin Titers: Significant Increase were used, as shown in Table 2, five male and five female of each strain.

The immediate and delayed hypersensitivity reactions were determined as described under the heading "3. Immediate and Delayed Hypersensitivity Reactions" above. The results are shown in Table 2, in which a "0" (zero) indicates that the footpad swelling was less than ten percent over the control, a "+" (plus sign) means that there was significant footpad swelling greater than ten percent over the control and a "–" (minus sign) means there was a significant suppression of footpad swelling greater than ten percent over the control.

The hemagglutinin titers were determined using the procedure described under the heading "4. Hemagglutinin Titers". The results are shown in Table 2.

EXAMPLE 3

PUSTULAN SULFATE

The dosage of pustulan sulfate was determined in toxicity studies as described under the heading "2. Toxicity Studies" above and the dosage was selected to be fifty milligrams per kilogram of body weight of

TABLE 2

ACYLATED PUSTULAN (used at 100 mg/kg body weight)

| Strain | Sex | First Challenge | | | Second Challenge | | |
|---|---|---|---|---|---|---|---|
| | | 4 hr | 24 hr | 48 hr | 4 hr | 24 hr | 48 hr |
| ESP | M | 0 | + | + | 0 | 0 | 0 |
| ESP | F | 0 | + | + | 0 | + | 0 |
| CFW | M | 0 | + | 0 | 0 | + | 0 |
| CFW | F | + | + | 0 | + | + | 0 |
| B6D2F1 | M | 0 | + | + | + | + | 0 |
| B6D2F1 | F | 0 | 0 | + | 0 | + | 0 |

Hemagglutinin Titers: Not Significant the mice. Three strains of mice were used, as shown in Table 3, five male and five female of each strain.

The immediate and delayed hypersensitivity reactions were determined as described under the heading "3. Immediate and Delayed Hypersensitivity Reactions" above. The results are shown in Table 3, in which a "0" (zero) indicates that the footpad swelling was less than ten percent over the control, a "+" (plus sign) means that there was significant footpad swelling greater than ten percent over the control and a "–" (minus sign) means there was a significant suppression of footpad swelling greater than ten percent over the control.

The hemagglutinin titers were determined using the procedure described under the heading "4. Hemagglutinin Titers". The results are shown in Table 3.

Groups of ten mice were immunized subcutaneously with fifty micrograms of ovalbumin for each kilogram of body weight, with each group being a different of the three species and five of each group being male and five female. A control group was given only the ovalbumin at a dose of forty micrograms for each kilogram of body weight and the experimental group was given pustulan sulfate at a dose of one hundred

TABLE 3

PUSTULAN SULFATE (used at 50 mg/kg body weight)

| Strain | Sex | First Challenge | | | Second Challenge | | |
|---|---|---|---|---|---|---|---|
| | | 4 hr | 24 hr | 48 hr | 4 hr | 24 hr | 48 hr |
| ESP | M | 0 | + | + | + | + | + |
| ESP | F | 0 | + | + | 0 | + | + |
| CFW | M | 0 | 0 | + | 0 | + | + |
| CFW | F | + | + | + | 0 | + | 0 |
| B6D2F1 | M | — | + | 0 | + | + | 0 |
| B6D2F1 | F | 0 | + | + | 0 | + | 0 |

Hemagglutinin Titers: Significant Increase micrograms per kilogram of body weight, following procedure 6 above under the heading "6. Active Systemic Anaphylaxis". The results are shown in Table 4.

EXAMPLE 4

MYCODEXTRAN

The dosage of mycodextran was determined in toxicity studies as described under the heading "2. Toxicity Studies" above and the dosage was selected to be fifty milligrams per kilogram of body weight of the mice. Three strains of mice were used, as shown in Table 5, five male and five female of each strain.

The immediate and delayed hypersensitivity reactions were determined as described under the heading "3. Immediate and Delayed Hypersensitivity Reactions" above. The results are shown in Table 5, in which a "0" (zero) indicates that the footpad swelling was less ten percent over the control, a "+" (plus sign) means that there was significant footpad swelling greater than ten percent over the control and a "–" (minus sign) means there was a significant suppression of footpad swelling greater than ten percent over the control.

TABLE 4

OVALBUMIN-INDUCED ANAPHYLACTIC SHOCK
Effect of Pustulan Sulfate
on Anaphylactic Shock in Mice
Percent Survivors

| ESP | | CFW | | B6D2F1 | |
|---|---|---|---|---|---|
| Male | Female | Male | Female | Male | Female |
| Control Group Given Ovalbumin Only | | | | | |
| 90 (9/10) | 70 (7/10) | 0 (0/10) | 80 (8/10) | 100 (10/10) | 100 (10/10) |
| Experimental Group Given Ovalbumin Plus Pustulan Sulfate | | | | | |
| 10 (1/10) | 40 (4/10) | 30 (3/10) | 20 (2/10) | 100 (10/10) | 100 (10/10) |

TABLE 5

MYCODEXTRAN

| Strain | Sex | First Challenge | | | Second Challenge | | |
|---|---|---|---|---|---|---|---|
| | | 4 hr | 24 hr | 48 hr | 4 hr | 24 hr | 48 hr |
| ESP | M | 0 | + | 0 | 0 | 0 | 0 |
| ESP | F | 0 | + | 0 | 0 | 0 | 0 |
| CFW | M | + | 0 | 0 | 0 | 0 | 0 |
| CFW | F | 0 | 0 | + | 0 | + | + |
| B6D2F1 | M | + | 0 | + | + | + | + |
| B6D2F1 | F | — | + | 0 | 0 | 0 | + |

Hemagglutinin Titers: Not Significant

The hemagglutinin titers in Table 5 were determined using the procedure described under the heading "4. Hemagglutinin Titers."

EXAMPLE 5

MYCODEXTRAN SULFATE

The dosage of mycodextran sulfate was determined in toxicity studies as described under the heading "2. Toxicity Studies" above and the dosage was selected to be fifty milligrams per kilogram of body weight of mice. Three strains of mice were used, as shown in Table 6, five male and five female of each strain.

The immediate and delayed hypersensitivity reactions were determined as described under the heading "3. Immediate and Delayed Hypersensitivity Reactions" above. The results are shown in Table 6, in which a "0" (zero) indicates that the footpad swelling was less than ten percent over the control, a "+" (plus sign) means that there was significant footpad swelling greater than ten percent over the control and a "−" (minus sign) means there was a significant suppression of footpad swelling greater than ten percent over the control.

TABLE 6

MYCODEXTRAN SULFATE

| | | First Challenge | | | Second Challenge | | |
|---|---|---|---|---|---|---|---|
| Strain | Sex | 4 hr | 24 hr | 48 hr | 4 hr | 24 hr | 48 hr |
| ESP | M | 0 | + | + | 0 | + | 0 |
| ESP | F | 0 | + | + | 0 | + | 0 |
| CFW | M | 0 | + | 0 | + | + | + |
| CFW | F | 0 | + | + | + | + | 0 |
| B6D2F1 | M | 0 | + | + | 0 | + | 0 |
| B6D2F1 | F | + | + | + | 0 | + | 0 |

Hemagglutinin Titers: Not Significant

The hemagglutinin titers were determined using the procedure described under the heading "4. Hemagglutinin Titers". The results are shown in Table 6.

Groups of ten mice were immunized subcutaneously with fifty micrograms of ovalbumin. Each group of ten mice is a different strain of the three above-mentioned strains of mice, with five of the mice in each group being male and five female. A control group was given only the ovalbumin at a dose of forty milligrams per kilogram of body weight and the experimental group was given mycodextran sulfate at a dose of fifty milligrams per kilogram of body weight, following procedure 6 above under the heading "6. Active Systemic Anaphylaxis." The results are shown in Table 7. Similar groups of ten mice were immunized with ovalbumin and an adjuvant and bled from the retroorbital venous plexus, following procedure 7 under the heading "7. Passive Cutaneous Anaphylaxis (PCA)" above, to determine systemic active anaphylaxis. The results are shown in Table 7.

EXAMPLE 6

MYCODEXTRAN SULFATE IN RATS

The dosage of mycodextran sulfate was determined in toxicity studies as described under the heading

TABLE 7

OVALBUMIN-INDUCED ANAPHYLACTIC SHOCK
Effect of Mycodextran Sulfate
on Anaphylaxis in Mice
Percent Survivors

| ESP | | CFW | | B6D2F1 | |
|---|---|---|---|---|---|
| Male | Female | Male | Female | Male | Female |
| Control Group Given Ovalbumin Only | | | | | |
| 70 (7/10) | 100 (10/10) | 100 (10/10) | 100 (10/10) | 100 (10/10) | 100 (10/10) |
| Experimental Group Given Ovalbumin Plus Mycodextran | | | | | |
| 60 (6/10) | 70 (7/30) | 0 (0/10) | 0 (0/10) | 100 (10/10) | 100 (10/10) |

"2. Toxicity Studies" above and the dosage was selected to be fifty milligrams per kilogram of body weight of the rats. The strain of rats used is as shown in Table 8, five male and five female rats were used.

The immediate and delayed hypersensitivity reactions were determined as described under the heading "3. Immediate and Delayed Hypersensitivity Reactions" above. The results are shown in Table 8, in which a "0" (zero) indicates that the footpad swelling was less than ten percent over the control, a "+" (plus sign) means that there was significant footpad swelling greater than ten percent over the control and a "−" (minus sign) means there was a significant suppression of footpad swelling greater than ten percent over the control.

The hemagglutinin titers were determined using the procedure described under the heading "4. Hemagglutinin Titers." The results are shown in Table 8.

EXAMPLE 7

PUSTULAN SULFATE

The dosage of pustulan sulfate was determined in toxicity studies as described under the heading "2.

TABLE 8

MYCODEXTRAN EXPERIMENTS IN RATS
MYCODEXTRAN SULFATE

| | | First Challenge | | |
|---|---|---|---|---|
| Strain | Sex | 4 hr | 24 hr | 48 hr |
| COBS CDF | M | 0 | + | 0 |
| COBS CDF | F | 0 | + | 0 |

Hemagglutinin Titers: Significant Increase in Male and Female Rats

Toxicity Studies" above and the dosage was selected to be fifty milligrams per kilogram of body weight of the mice. Three strains of mice were used, as shown in Tables 9–14, five male and five female of each strain.

The immediate and delayed hypersensitivity reactions were determined as described under the heading "3. Immediate and DHR (Delayed Hypersensitivity Reactions) above. The results are shown in Tables 9–14, in which a "0" (zero) indicates that the footpad swelling was less than ten percent over the control, a "+" (plus sign) means that there was significant footpad swelling greater than ten percent over the control and a "−" (minus sign) means there was a significant suppression of footpad swelling greater than ten percent over the control.

The hemagglutinin titers were determined using the procedure described under the heading "4. Hemagglutinin Titers". The results are shown in Table 15.

EXAMPLE 8

In tests for selective enhancement of footpad swelling cell-mediated response without allograft

TABLE 9

| | | Hypersensitivity Immediate Type | | |
|---|---|---|---|---|
| Strain | Sex | Adjuvant Effect | No Effect | Suppress Effect |
| ESP | M | | x | |
| ESP | F | | x | |

TABLE 9-continued

| | | Hypersensitivity Immediate Type | | |
|---|---|---|---|---|
| Strain | Sex | Adjuvant Effect | No Effect | Suppress Effect |
| CFW | M | | x | |
| CFW | F | x slight | | |
| B6D2F1/J | M | | | x slight |
| B6D2F1/J | F | x | | |

TABLE 10

| | | Hypersensitivity Immediate Type | | |
|---|---|---|---|---|
| Strain | Sex | Adjuvant Effect | No Effect | Suppress Effect |
| ESP | M | x | | |
| ESP | F | | x | |
| CFW | M | | x | |
| CFW | F | | x | |
| B6D2F1/J | M | x | | x |
| B6D2F1/J | F | | | x |

TABLE 11

| | | Hypersensitivity 24-Hr Delayed Type | | |
|---|---|---|---|---|
| Strain | Sex | Adjuvant Effect | No Effect | Suppress Effect |
| ESP | M | x | | |
| ESP | F | x | | |
| CFW | M | | | x |
| CFW | F | x | | |
| B6D2F1/J | M | x | | |
| B6D2F1/J | F | x | | |

TABLE 12

| | | Hypersensitivity 24-Hr Delayed Type | | |
|---|---|---|---|---|
| Strain | Sex | Adjuvant Effect | No Effect | Suppress Effect |
| ESP | M | x | | |
| ESP | F | x | | |
| CFW | M | x | | |
| CFW | F | x | | |
| B6D2F1/J | M | | | |
| B6D2F1/J | F | x | | |

TABLE 13

| | | Hypersensitivity 48-Hr Delayed Type | | |
|---|---|---|---|---|
| Strain | Sex | Adjuvant Effect | No Effect | Suppress Effect |
| ESP | M | x | | |
| ESP | F | x | | |
| CFW | M | x | | |
| CFW | F | x | | |
| B6D2F1/J | M | | x | |
| B6D2F1/J | F | x | | |

TABLE 14

| | | Hypersensitivity 48-Hr Delayed Type | | |
|---|---|---|---|---|
| Strain | Sex | Adjuvant Effect | No Effect | Suppress Effect |
| ESP | M | x | | |
| ESP | F | x | | |
| CFW | M | x | | |
| CFW | F | | x | |
| B6D2F1/J | M | | x | |
| B6D2F1/J | F | | x | |

TABLE 15

PUSTULAN SULFATE IN MICE

| | | Hemagglutinin Titers | |
|---|---|---|---|
| Strain | Dosage | Pre-Challenge | Post-Challenge |
| ESP | 50 mg/kg | 2 | 512 |
| ESP | Control | 0 | 256 |
| ESP | 50 mg/kg | 0 | 512 |
| ESP | Control | 2 | 256 |
| CFW | 50 mg/kg | 0 | 256 |
| CFW | Control | 2 | 32 |
| CFW | 50 mg/kg | 4 | 256 |
| CFW | Control | 4 | 256 |
| B6D2F1/J | 50 mg/kg | 2 | 512 |
| B6D2F1/J | Control | 2 | 128 |
| B6D2F1/J | 50 mg/kg | 2 | 512 |
| B6D2F1/J | Control | 2 | 128 | rejection cell-mediated response, four doses of the pustulan sulfate were studied: 25 mg/kg, 50 mg/kg, 100 mg/kg and 200 mg/kg of body weight using the procedures described with respect to Examples 1–8. Toxicity for the three strains of mice tested are shown in Table 16.

In these tests, groups of five mice were injected subcutaneously in the scruff of the neck with the indicated dose, observed for seven days and sacrificed for autopsy. At the doses of 100 mg/kg and 200 mg/kg pustulan sulfate was shown to be toxic. Only five of the thirty mice tested with 200 mg/kg survived through day seven. Four of the thirty mice tested with a 100 mg/kg dose died before day seven. Two of the 26 surviving animals of this group were found to have subcutaneous scarring at the injection site.

At the lower dose of 25 mg/kg, no deaths occurred and no toxic effects were found. At 50 mg/kg, no deaths occurred and only two of the animals tested showed subcutaneous scarring. The 50 mg/kg dose was chosen for use in in vivo studies.

Tests for footpad swelling of mice due to SRBC alone and SRBC with pustulan sulfate were made with mice sensitized with SRBC and experimental mice

TABLE 16

Pustulan Sulfate Toxicity Study

| strain | sex | dose mg/kg body weight | at day 7 deaths | animals with subcutaneous scars per # of survivors |
|---|---|---|---|---|
| CFW | m | 25 | 0 | 0/5 |
| CFW | f | 25 | 0 | 0/5 |
| CFW | m | 50 | 0 | 0/5 |
| CFW | f | 50 | 0 | 0/5 |
| CFW | m | 100 | 0 | 0/5 |
| CFW | f | 100 | 0 | 0/5 |
| CFW | m | 200 | 4 | 0/1 |
| CFW | f | 200 | 5 | 0/0 |
| ESP | m | 25 | 0 | 0/5 |
| ESP | f | 25 | 0 | 0/5 |
| ESP | m | 50 | 0 | 2/5 |
| ESP | f | 50 | 0 | 0/5 |
| ESP | m | 100 | 1 | 4/5 |
| ESP | f | 100 | 0 | 2/5 |
| ESP | m | 200 | 4 | 0/1 |
| ESP | f | 200 | 3 | 0/2 |
| BDF | m | 25 | 0 | 0/5 |
| BDF | f | 25 | 0 | 0/5 |
| BDF | m | 50 | 0 | 0/5 |
| BDF | f | 50 | 0 | 0/5 |
| BDF | m | 100 | 1 | 0/4 |
| BDF | f | 100 | 2 | 0/3 |
| BDF | m | 200 | 5 | 0/0 |
| BDF | f | 200 | 5 | 0/0 | injected with SRBC and pustulan sulfate. P values less than 0.05 were considered significant. Values were calculated using Student's t-test for the difference between two means.

All strains of mice tested showed an increased DTH reaction to SRBC when pustulan sulfate was administered at the time of sensitization as shown in Table 17. All strains showed a significant increase in footpad swelling over controls at 24 hours after the first challenge with one exception (male CFW mice did not show a statistically significant increase due to wide variance between individuals of the group, although pronounced swelling was observed). Increases in 48 hour swellings occurred, but results varied from strain to strain and from male to female of the same strain. Increased DTH responses were also noted after the second challenge in all but ESP male m ice.

Survival times of allogenic skin grafts were not altered from controls as shown in Table 18. This result was consistent in the three dosage and treatment schedules tested. The free skin grafting technique described in the publication of Billingham & Medawar (1951) "The Technique of Free Skin Graftings in Mammals" *J. Exp. Biol.*, 28:385–402, the

TABLE 17

Effect of Pustulan Sulfate on Footpad Swelling Responses

| Strain | Sex | Group | Group Mean % Change | | % Increase over Controls | | P Value | |
|---|---|---|---|---|---|---|---|---|
| | | | 24 hours | 48 hours | 24 hours | 48 hours | 24 hours | 48 hours |
| BDF | M | con | 24.5 | 10.1 | — | — | — | — |
| | | exp | 41.7 | 16.2 | 17.2 | 6.1 | 0.049 | 0.08 |
| BDF | F | con | 22.7 | 9.1 | — | — | — | — |
| | | exp | 55.9 | 22.8 | 33.2 | 13.7 | 0.001 | 0.005 |
| ESP | M | con | 13.1 | 8.2 | — | — | — | — |
| | | exp | 44.2 | 24.1 | 31.1 | 15.9 | 0.001 | 0.001 |
| ESP | F | con | 34.4 | 17.5 | — | — | — | — |
| | | exp | 51.1 | 29.7 | 16.7 | 12.2 | 0.006 | 0.01 |
| CFW | M | con | 18.4 | 13.1 | — | — | — | — |
| | | exp | 34.4 | 21.1 | 6.0 | 8.0 | 0.44 | 0.09 |
| CFW | F | con | 26.9 | 9.6 | — | — | — | — |
| | | exp | 45.8 | 23.1 | 18.9 | 13.5 | 0.002 | 0.004 |

TABLE 18

Effect of Pustulan Sulfate on Allogeneic Skil Graft Rejection

| Group # | Dose, mg/kg Body Weight | Animals per Group | Treatment | Mean Days to Rejection | S.E. |
|---|---|---|---|---|---|
| 1 | — | 11 | control, graft only | 13.5 | 0.92 |
| 2 | 50 | 10 | 1 dose with graft | 14 | 0.44 |
| 3 | 5 | 11 | daily i.p., 5 days prior to grafting through rejection | 12.75 | 0.53 |
| 4 | 5 | 10 | daily i.p., day of grafting through rejection | 13.29 | 0.52 | disclosure of which is incorporated herein, was used in all experiments. Donor skin was taken from C3H/HeJ male mice and grafted to CFW male mice. Criteria for rejection have been described in the publication of Babcock, et al., (1977) "Suppression of Cell-Mediated Immune responses by Dextran Sulphate", *Immunology*, 33:925–929, the disclosure of which is incorporated herein.

EXAMPLE 9

LEUKEMIA P388

GENERAL

In tests to determine increase in mouse survival time in mice innoculated with mouse leukemia P388 with the use of mycodextran sulfate, five doses of mycodextran sulfate were studied, which are: 100 mg/kg (milligram for each kilogram of body weight using the procedures described with respect to examples 1–8); 50 mg/kg; 25 mg/kg; 12.5 mg/kg; and 6.25 mg/kg. These doses were applied to each of eight B6d2f1/j male mice, 12 weeks old, and having weights within three grams of each other. In the control group, thirty mice were used.

The mice were injected interparietally with tumor cells conventionally designated as P-388 having 106 cells for each 0.1 milliliter HBSS injected at the start of the test. For a positive control, the same tumor cells were injected into eight of the same strain of mice, for a negative control it was injected into 30 mice of the same strain and it was injected into eight mice who were also injected with a saline solution. The materials were prepared in sterile saline and injected interparietally within 15 minutes in a solution of 0.02 milliliters per gram of mouse body weight for nine days.

The results are shown in Table 19. The experiment was repeated without applying a dosage of 100 mg/kg because of the number of toxic deaths at this number and the results are shown in Table 20. The median survival rate was calculated by adding the number of days expired until the total number of deaths in a group is half of the mice in the group to the earliest day when the cumulative number of deaths is one more than half of the number of mice in the group divided by two. The test to control ratio (t/c) is significant when it is above 125 percent (test group median survival time divided by the negative control median survival time multiplied by 100). The toxic deaths are the number of mice in each group which died before day six.

TABLE 19

| Experimental Group | Anti-Tumor Agent | Dosage (mg/kg) | Median Survival | T/C 70 | Toxic deaths |
|---|---|---|---|---|---|
| 1 | MS | 100 | 3.0 | 22 | 7 |
| 2 | MS | 50 | 10.5 | 77 | 4 |
| 3 | MS | 25 | 19.5 | 144 | 2 |
| 4 | MS | 12.5 | 17.0 | 126 | 0 |
| 5 | MS | 6.25 | 16.0 | 119 | 0 |
| 6 | 5-FU | 20 | 25.0 | 185 | 0 |
| 7 | Saline |  | 15.5 | 115 | 0 |
| 8 | None (Neg Cont) |  | 13.5 |  | 0 |

TABLE 20

| Experimental Group | Anti-Tumor Agent | Dosage (mg/kg) | Median Survival | T/C 70 | Toxic deaths |
|---|---|---|---|---|---|
| 1 | MS | 50 | 21.5 | 179 | 2 |
| 2 | MS | 25 | 15.5 | 129 | 1 |
| 3 | MS | 12.5 | 18.5 | 154 | 0 |
| 4 | MS | 6.25 | 14.0 | 117 | 0 |
| 5 | 5-FU | 20 | 19.5 | 163 | 0 |
| 6 | Saline |  | 11.5 | 95 | 0 |
| 7 | None (Neg Cont) |  | 12.0 |  | 0 |

From these tests, it can be seen that doses of mycodextran sulfate at non-toxic levels above a threshold, which was 6.25 milligrams per kilogram of weight in the above tests have shown anti-tumor activity.

EXAMPLE 10

DETERMINATION OF BINDING SITES

To prepare single cell suspensions: (1) mice were sacrificed by cervical dislocation; (2) spleens were dissected out and placed in a 10×35 millimeter plastic petri dish with five milliliter of phosphate buffered saline and five percent PBS, at 4 degrees Centigrade and pH 7.1 to 7.2; (3) cells were removed from the organ; (4) the removed cells were washed by suspending in a medium and decanting; (5) the red cells were lysed and the suspension washed; and the spleen cell suspension prepared.

To remove and wash the cells: (1) a cell suspension was made by squashing the organ between the frosted ends of two microscope slides and rinsing the slides with the medium in the petri dishes; (2) the cells and medium were transferred by Pasteur pipette to 12×75 millimeter glass tubes, leaving the capsule in the petri dish; (3) debris was allowed to settle for 5 minutes; (4) supernatant was transferred by Pasteur pipette to a clean 12×75 millimeter tube; and (5) the cells were spun down at 300 gravity for five minutes at 4 degrees Centigrade.

To separate and prepare the single-cell suspension of spleen cells, the supernatant was poured off and red cells were lysed by mixing the pellet for 15 seconds with 0.5 milliliters distilled water. Lysing was stopped by the addition of 3.5 milliliters of medium and the cells were spun as above and washed twice with four milliliters of medium. After the final wash, spleen cells were resuspended in one to two milliliters of RPMI 1640+Hepes, depending on pellet size. An aliquot of the cells was stained, counted and viability was assessed by the trypan blue dye exclusion method. All preparations used contained ninety percent or more viable cells. Suspensions were adjusted to $5\times10^6$ cells/ml.

Membrane binding studies were performed using techniques described in the publication of Paul, Maragnos & Skolnick (1981) cited earlier with the following modifications. Total binding of tritiated pustulan sulfate to cells was determined by incubating 100 ul (microliters) 500,000 cells of a single cell suspension with 50 ul of media and 50 ul of tritiated pustulan sulfate in a flat bottom microtiter plate (Flow Laboratories, Inc., McLean, Va.).

The concentrations of tritiated pustulan sulfate examined ranged from ten nanograms added/well to 400 ng/well. Non-specific binding to cells was determined by incubating 100 microliters of cells with 50 microliters tritiated pustulan sulfate (ranging from 10 ng/well to 400 ng/well) and 50 microliter of parent compound (1 microgram added per well).

The reaction was terminated by separating bound and free ligand by collecting cells on glass fibre filters (Whatman, Clinton, N.J.) with two quick rinses using a cell harvester (Otto Hiller Co., Madison, Wis.). Radioactive ligand was detected by placing dried filter discs in seven milliliters of scintillation cocktail (Hydrocount, J. L. Baker), mixing and then standing for at least 1 hour and counting with a Beckman LS7500 LSC using an appropriate program for tritium detection.

Specific binding values may be calculated as the difference between total and non-specific binding. The total ligand (tritiated pustulan sulfate) bound was determined by incubating cells and radiolabeled compound in RPMI-1640 +Hepes for 1 hour at 4 degrees Centigrade. Non-specific binding was determined in a similar manner with the addition of a large excess of non-labeled compound. The amount of specific ligand bound is computed as the difference between total and non-specific ligand bound. P values less than 0.05 were considered significant. Values were computed using Student's t-test for the difference between two means. The results are shown in Table 19.

As indicated in Table 21, low levels of specific binding were consistently detected. Results for one experiment in Table 21 are representative of three separate experiments. Specific binding was detected in the three experiments in wells with tritiated pustulan sulfate concentration levels ranging from 10 to 100 ng/well. Specific binding at 200/well is detectable, but is not consistently found. When higher concentrations of radioactive pustulan sulfate are added, non-specific binding levels increase sharply and no specific binding is detectable.

For toxicity studies with pustulan at 50, 100, 200 or 400 milligrams per kilogram of body weight, some local inflammation at the injection site is observed. For pustulan sulfate at 25, 50, 100 or 200 milligrams per kilogram of body weight, no toxicity

TABLE 21

| Spleen Cell Membrane Binding of Pustulan Sulfate (PS) | | | | |
|---|---|---|---|---|
| ng added | total PS bound* | non-specific PS bound | p value | specific PS bound |
| 10 | 859 | 768 | 0.013 | 91 |
| 50 | 5033 | 4555 | 0.024 | 443 |
| 100 | 9560 | 9219 | 0.038 | 341 |

*bound ligand expressed as decay per minute (dpm)

is observed at 25 or 50 milligrams per kilogram of body weight but toxic effects and some deaths are observed in animals receiving 100 or 100 milligrams per kilogram of body weight.

In the delayed hypersensitivity response-footpad swelling test, the 24 and 48 hour delayed hypersensitivity responses with pustulan sulfate adjuvant are indicated in Tables 11–14. The results indicate that there was a response by five or six groups of animals at 24 and 48 hours after the first challenge. Following the second challenge, five of six groups of mice indicate a significant delayed hypersensitivity response.

There are some increases in titers of hemagglutinating antibodies in the animals receiving pustulan sulfate. The results are shown in Table 15. There were no deaths from anaphylactic shock in the groups of animals following the first challenge with antigen. Five of ten male ESP mice died following the second challenge. No signs of shock were observed in the remaining animals. Pustulan sulfate exerts significant adjuvant action in the system employed. The effect is greatest on the delayed hypersensitivity reaction. Changes in immunoglobulin synthesis are minimal. Pustulan sulfates selectively enhance one delayed immune response (footpad swelling) but not another (allograft rejection) and show specific binding sites. The amount of specific binding is approximately 5 percent which corresponds to the percentage of T4 helper cells available for attachment to virus parts such as by the HIV glycoprotein attachment to the cellular protein of the helper T4 cells. The suppression of virus in the HIV family is discussed in "Dextran Sulfate Suppression of Viruses in the HIV Family: Inhibition of Virion Binding to CD4+Cells" by Mitsuya et al., *Science*, v. 240, pp. 646–649.

Each of the classes of high-molecular-weight polysaccharides is either inert in its unsulfated condition or produces minimal immunological response changes and is an active immunoregulator following sulfation. The degree of sulfation may be modulated in such a way that the compounds have all available sites saturated that accept the sulfate or have partial sulfation. Complete sulfation results in the greatest immunoregulatory effect while moderate sulfation yields a lesser immunoregulataory effect in the case of such modulation.

The results of this study are summarized in Tables 1 through 19 and are consistent with the prior results of studies on dextran sulfate as reported by R. E. McCarthy, L. W. Arnold and G. F. Babcock in *Immunology*, 1977, 32, pp.963–974, entitled "Dextran Sulphate: An Adjuvant for Cell-mediated Immune Responses," the disclosure of which is incorporated herein for reference.

Non-acylated pustulan, (i.e., pustulan molecule with no substitutent groups,) has a certain degree of regulatory effect in that the delayed hypersensitivity footpad swelling response is increased significantly at 24 hours following both first and second challenges with antigen. Acylated pustulan, the form in which it is commercially available, is seen to have a positive effect on the delayed footpad swelling reaction, which in general is greater than that observed for the unsubstituted pustulan molecule. Pustulan sulfate is observed to have an even greater effect on the immune response than either of the other two forms of pustulan. The effect of pustulan sulfate on anaphylactic shock reactions in mice is reported in Table 4.

The incidence of fatal anaphylaxis in ESP and CFW mice is greatly increased when pustulan sulfate is used as an adjuvant. The B6D2F1 strain of animal is extremely resistant to the induction of anaphylaxis under any circumstances and it has been our experience to date that no compound acts as an anaphylactic shock inducer in this strain.

The results of experiments with mycodextran are reported in Tables 5 through 8. Unsubstituted mycodextran has a minimal effect on the immune responses as indicated by changes in footpad swelling reaction. Sulfation (Tables 6 and 7) converts this material into a highly active immunoregulator. Moreover, mycodextran sulfate has a significant effect on delayed hypersensitivity responses in rats as well (Table 8). The effect of mycodextran sulfate on anaphylaxis in mice is presented in Table 7. This compound has its greatest effect in CFW mice, in which there was one hundred percent lethality.

While experimental work has been done with SRBC because it is an accepted antigen, antigens other than SRBC may be used. For example, antigens used to assess whether there is diminished delayed hypersensitivity or anergy in selected patients may be among one of the following: (1) Candidin; (2) Mixed respiratory vaccine such as: (a) *Staphylococcus auareus*, (b) *Streptococcus*, (c) *Streptococcus pneumonia*, (d) *Neisseria catarrhalis*, (e) *Klebsiella pneumoniae* or (f) *Haemophilus influenzae*; (3) Purified protein derivative of tuberculin (PPD); (4) *Strephtokinase-streptodornase* (SK-50); (5) Syaphylococcal antigens (Staphage Lystate); (6) Trichophytin; or (7) Mumps virus.

If use of the above antigen produces a negative response, the following have been used to sensitize the patient and later test for response: (1) Dinitrochlorobenzene (DNCB); or (2) Keyhole limpet hemocyanin. These proceedings have been disclosed in Spitlet, Lynne E., 1980, "Delayed Hypersensitivity Skin Testing." *Manual of Criminal Immunology* (M. R. Rose and H. Friedman, Esq), American Society for Microbiology, Washington, D.C., pp.200–212.

As can be understood from the above description, the immunoregulators of this invention and its methods of use and preparation have several advantages, such as: (1) They can be used for T-cell-mediated responses only and thus reduce anaphylactic shock; (2) specific synthetic regulators are available to operate in a predictable manner; (3) it is possible to use a dosage and regulator for a known type of response; and (4) it is possible to synthesize regulators for particular antigens.

Although a preferred embodiment has been described with some particularity, many modifications and variations may be made in the preferred embodiment without deviating from the invention. Accordingly, it is to be understood that, within the scope of the appended claims, the invention may be practiced other than as specifically described.

What is claimed is:

1. A method for reducing hypersensitivity reactions and anaphylactic shock comprising the steps of:

obtaining an immunoregulator that stimulates immune responses to an antigen without anaphylactic shock, said immunoregulator comprising a polysaccharide compound having a molecular weight between 1,000 and 600,000 selected from a group consisting of sulfated mycodextran, sulfated pustulan and acylated pustulan wherein a polyanionic heavy-molecule regulator which is not cytotoxic is formed; and inoculating a subject having the antigen with a dose of the immunoregulator which is not toxic to the subject and which reacts selectively with a component of the subject's immune response system within a predetermined time of the appearance of an immune response in the subject caused by the antigen.

2. A method of reducing hypersensitivity reactions and anaphylatic shock when immunizing a subject having T4 helper cells activated by an antigen within a predetermined class of antigens comprising the steps of:

inoculating the subject with an immunoregulator which reacts selectively with the T4 cells of the subject that counteract that predetermined class of antigens; wherein the step of inoculating the subject includes the step of inoculating the subject with a polysaccharide having a molecular weight between 1,000 and 600,000 selected from a group consisting of sulfated mycodextran, sulfated pustulan and acylated pustulan; and inoculating the subject with an antigen within two days of injection with the immunoregulator.

3. A method of reducing hypersensitivity reactions and anaphylatic shock when using a therapy against an antigen comprising the step of inoculating the subject of the therapy with an immunoregulator which reacts selectively with T4 cells activated by the antigen, said immunoregulator comprising molecules having a molecular weight between 1,000 and 600,000 selected from a group consisting of sulfated mycodextran, sulfated pustulan and acylated pustulan.

4. A method according to claim 3 further comprising the step of inoculating the subject with a predetermined antigen within two days of injection with the immunoregulator.

5. A method according to claim 3 wherein the subject of the therapy is innoculated at intervals of at least one week.

* * * * *